United States Patent [19]

Bock et al.

[11] Patent Number: 4,663,310
[45] Date of Patent: May 5, 1987

[54] RENIN INHIBITORS CONTAINING 2-SUBSTITUTED STATINE

[75] Inventors: Mark G. Bock, Hatfield; Joshua S. Boger, Bryn Mawr; Stephen F. Brady, Philadelphia; Daniel F. Veber, Ambler, all of Pa.

[73] Assignee: Merck & Co., Inc., Rahway, N.J.

[21] Appl. No.: 596,766

[22] Filed: Apr. 4, 1984

[51] Int. Cl.⁴ .................. H61K 37/43; C07K 7/06
[52] U.S. Cl. .................. 514/15; 514/16; 514/17; 514/18; 530/328; 530/329; 530/330
[58] Field of Search .................. 260/112.5 R; 514/15, 514/16, 17, 18; 530/328, 329, 330

[56] References Cited

U.S. PATENT DOCUMENTS 4,185,096  1/1980  Castro et al. .................. 260/112.5 R
4,269,827  5/1981  Burton et al. .................. 260/112.5 R

FOREIGN PATENT DOCUMENTS 0077028  4/1983  European Pat. Off. .
0077029  4/1983  European Pat. Off. .
1587809  4/1981  United Kingdom .

OTHER PUBLICATIONS

Veber et al., Biochem. Soc. Trans., vol. 12, Part 6, 956–9 (1984).
J. Antibiot. (Tokyo), 23:259–262, 1970.
Gross et al., Science, 175:656, 1971.
Tewksbury et al., Circulation, 59, 60, Supp. II:132, 10/79.
Poulsen et al., Biochem. Biophys. Acta, 452:533–537, 1976.
Skeggs, Jr. et al., J. Exp. Med., 106:439–453, 1957.
Kokubu et al., Biochem. Pharmacol., 22:3217–3223, 1973.
Burton et al., Biochemistry, 14:3892–3898, 1975.
Poulsen et al., Biochemistry, 12:3877–3882, 1973.
Haber and Burton, Fed. Proc. Fed. Am. Soc. Exp. Biol., 38:2768–2773, 1979.
Szelke et al., Nature, 299, 555, 1982.
Szelke et al., Hypertension, 4, Supp. 2, 59, 1981.
Power et al., Acid Proteases, Structure, Function and Biology, Plenum Press, 1977, 141–157.
Tang et al., Trends in Biochem. Sci., 1:205–208, 1976.
Tang et al., J. Biol. Chem., 251:7088–94, 1976.
Rich, JACS, 104:3536–3537, 1982.
Chan et al., Tet. Lett., 4092, 1979.
Heathcock et al., J. Am. Chem. Soc., 99:247, 1977.
Heathcock et al., J. Org. Chem., 45:1727, 1980.
Frater, Helv. Chem. Acta, 62:2825, 1979.
Thomas et al., J. Chem. Soc. Chem. Comm., 1115, 1982.
Yamamoto, Tet. Lett., 2387, 1982.
Mulzer et al., Tet. Lett., 4651, 1977.
Mulzer et al., Ann., 1108, 1980.
Boger et al., Nature, 303:81–84, 1983.
Marshall, Federation Proc., 35:2494–2501, 1976.
Burton et al., Proc. Natl. Acad. Sci. USA, 77:5476–5479, 9/80.
Swales, Pharmac. Ther., 7:173–201, 1979.
Kokubu et al., Nature, 217:456–457, 2/3/68.
Matsushita et al., J. Antibiotics, 28:1016–1018, 12/75.
Lazar et al., Biochem. Pharma., 23:2776–2778, 1974.
Miller et al., Biochem. Pharma., 21:2941–2944, 1972.
Haber, Clinical Science, 59:7s–19s, 1980.
Rich et al., J. Org. Chem., 43:3624, 1978.
Rich et al., J. Med. Chem., 23:27, 1980.

Primary Examiner—Delbert R. Phillips
Attorney, Agent, or Firm—Richard A. Elder; Raymond M. Speer; Hesna J. Pfeiffer

[57] ABSTRACT

Renin inhibitory peptides of the formula

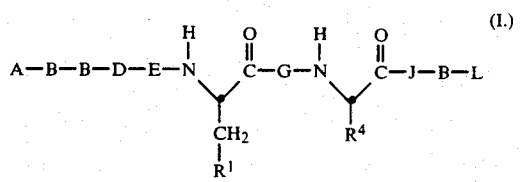

and analogs thereof inhibit renin and are useful for treating various forms of renin-associated hypertension and hyperaldosteronism.

4 Claims, No Drawings

RENIN INHIBITORS CONTAINING 2-SUBSTITUTED STATINE

BACKGROUND OF THE INVENTION

1. Field of The Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate te renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_i$):

| Class | $K_i$ (M) |
| --- | --- |
| Renin antibody | probably $10^{-6}$ |
| Pepstatin | $10^{-6} - 10^{-7}$ |
| Phospholipids | $10^{-3}$ |
| Substrate analogs | |
| Tetrapeptides | $10^{-3}$ |
| Octa- to tridecapeptides | $10^{-5} - 10^{-6}$ |

Umezawa et al., in *J. Antibiot.* (Tokyo) 23: 259–262, 1970, reported the isolation of a peptide from actinomyces that was an inhibitor of aspartyl proteases such as pepsin, cathepsin D, and renin. This peptide, known as pepstatin, was found by Gross et al., *Science* 175: 656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

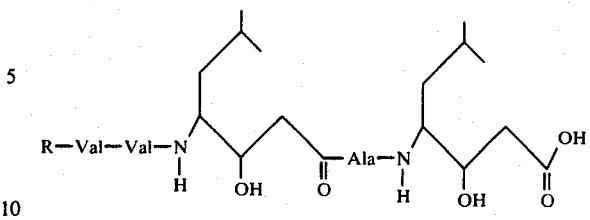

To date, many efforts have been made to prepare a specific renin inhibitor based on substrate analogy. Since the human renin substrate has only recently been elucidated (Tewksbury et al., *Circulation* 59, 60, Supp. II: 132, Oct. 1979), heretofore substrate analogy has been based on the known pig renin substrate. While the human and pig renin substrates are not the same, the substrate analogy based on pig renin has always been considered acceptable in the art as predictive of human renin inhibitory activity because of the closely related activity of the two renins. Thus, while pig renin does not cleave the human renin substrate, human renin, on the other hand, does cleave the pig renin substrate. See Poulsen et al., *Biochim. Biophys. Acta* 452: 533–537, 1976; and Skeggs, Jr. et al., *J. Exp. Med.* 106: 439–453, 1957. Moreover, the human renin inhibitory activity of the peptides of the present invention most active in inhibiting pig renin has been confirmed, thus providing further evidence of this accepted correlation between human and pig renin activity.

It has been found, for example, using pig renin substrate analogy, that the octapeptide sequence extending from histidine-6 through tyrosine-13 has kinetic parameters essentially the same as those of the full tetradecapeptide renin substrate. The amino acid sequence of the octapeptide in pig renin substrate is as follows:

```
  6    7    8    9   10   11   12   13
—His—Pro—Phe—His—Leu—Leu—Val—Tyr—
```

Renin cleaves this substrate between $Leu^{10}$ and $Leu^{11}$.

Kokubu et al., *Biochem. Pharmacol.* 22: 3217–3223, 1973, synthesized a number of analogs of the tetrapeptide found between residues 10 to 13, but while inhibition could be shown, inhibitory constants were only of the order of $10^{-3}$M.

Analogs of a larger segment of renin substrate were also synthesized: Burton et al., *Biochemistry* 14: 3892–3898, 1975, and Poulsen et al., *Biochemistry* 12: 3877–3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, *Fed. Proc. Fed. Am. Soc. Exp. Biol.* 38: 2768–2773, 1979.

More recently, Szelke et al., in work described in European Patent Publication No. 45,665; *Nature*, 299, 555 (1982); *Hypertension*, 4, Supp. 2, 59, 1981; British Patent No. 1,587,809; and "Novel Transition-State Analogue Inhibitors of Renin", a presentation at the Eighth American Peptide Symposium, May 22-27, 1983, Tucson, Ariz., have replaced the Leu-Leu site of renin cleavage by isosteric substitution, and obtained compounds with excellent potency.

Powers et al., in *Acid Proteases, Structure, Function and Biology*, Plenum Press, 1977, 141-157 have suggested that in pepstatin, statine occupies the space of the two amino acids on either side of the cleavage site of a pepsin substrate, and Tang et al., in *Trends in Biochem. Sci.*, 1: 205-208 (1976) and *J. Biol. Chem.*, 251: 7088-94, 1976, have proposed that the statine residue of pepstatin resembles the transition state for pepsin hydrolysis of peptide bonds. However, the applicability of these concepts to renin inhibitors is not taught in any of these references, and would be speculative due to the known high degree of specificity of the renin enzyme.

Rich, *JACS* 104: 3536—3537, 1982, describes (α-dimethylsulfonium statine)-containing peptides which inhibit pepsin; but does not disclose or suggest the renin inhibitors of the present invention.

Formation of carbon-carbon bonds by processes related to aldol condensation are described in the following references, none of which, however, describe or suggest preparation of 2-substituted statines or their use in forming renin inhibitors: Chan et al., *Tet. Lett.* 4092, 1979; Heathcock et al., *J. Am. Chem. Soc.*, 99: 247, 1977, and *J. Org. Chem.* 45: 1727, 1980; Frater, *Helv. Chim. Acta* 62: 2825; 1979; Thomas et al., *J. Chem. Soc. Chem. Comm.* 1115, 1982; Yamamoto, *Tet. Lett.* 2387, 1982; Mulzer et al., *Tet. Lett.* 4651, 1977, and *Ann.* 1108, 1980.

Veber and Rich, in U.S. Pat. No. 4,384,994 and published European Patent Application No. 0,077,029; Evans and Rittle, in U.S. Pat. No. 4,397,786; Veber and Boger, in published European Patent Application No. 0,077,028; Boger et al, *Nature*, 303: 81-84 (1983); have all described renin inhibitory peptides containing statine. However, none of these references describe or suggest the renin inhibitors containing 2-substituted statine of the present invention and the significant increase in renin inhibitory activity obtainable therewith.

For other articles describing previous efforts to devise renin inhibitors, see Marshall, *Federation Proc.* 35: 2494-2501, 1976; Burton et al., *Proc. Natl. Acad. Sci. USA* 77: 5476-5479, Sept. 1980; Suketa et al., *Biochemistry* 14: 3188, 1975; Swales, *Pharmac. Ther.* 7: 173-201, 1979; Kokubu et al., *Nature* 217: 456-457, Feb. 3, 1968; Matsushita et al., *J. Antibiotics* 28: 1016-1018, Dec. 1975; Lazar et al., *Biochem. Pharma.* 23: 2776-2778, 1974; Miller et al., *Biohem. Pharma.* 21: 2941-2944, 1972; Haber, *Clinical Science* 59: 7s-19s, 1980; Rich et al., *J. Org. Chem.* 43: 3624, 1978, and *J. Med. Chem.* 23: 27, 1980; Burton et al., U.S. Pat. No. 4,269,827; Castro et al., U.S. Pat. No. 4,185,096; and Sankyo Jap. Pat. No. 76-067001.

DETAILED DESCRIPTION OF THE INVENTION AND PREFERRED EMBODIMENTS

In accordance with the present invention there are provided renin inhibitory peptides of the formula:

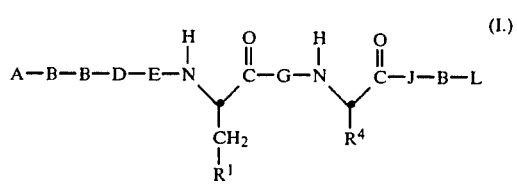

wherein:
A is hydrogen; or

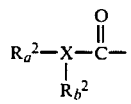

where X is $$-O-;\ -O-CH-;\ -CH-O-;\ -CH-;\ -NH-CH-;$$

$$\text{or}\ -S-CH-;$$

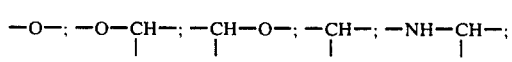

and $R_a^2$ and $R_b^2$ may be the same or different and are hydrogen; $W-(CH_2)_n-$ or $W-(CH_2)_m-CH=CH-(CH_2)_p$, where W is hydrogen; $C_{1-4}$ alkyl; aryl; $C_{3-7}$ cycloalkyl; or $C_{3-7}$ cycloalkyl or aryl substituted with up to five members independently selected from the group consisting of $C_{1-8}$ alkyl, trifuloromethyl, hydroxy, $C_{1-4}$ alkoxy, and halo; n is 0 to 5; m is 0 to 2; and p is 0 to 2; except that where X is $-O-$, only one of $R_a^2$ or $R_b^2$ is present;

B is absent; gylcyl; sarcosyl; or

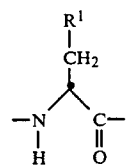

where $R^1$ is as defined further below;
D is absent; or

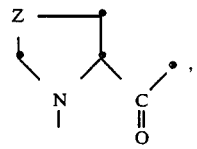

where Z is $-(CH_2)_l-$ and l is 1 or 2; or $-S-$;
E is absent; or

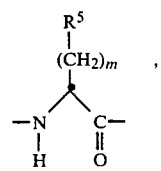

where m is 1 to 4; and $R^5$ is hydrogen; $C_{1-4}$ alkyl; aryl; aryl-$C_{1-4}$ alkyl; aryl $C_{1-4}$ alkyl or aryl where the aryl portion is substituted with up to three members selected from the group consisting of $C_{1-4}$ alkyl, trifluoromethyl, hydroxy, $C_{1-4}$ alkoxy, and halo; or indolyl;

G is

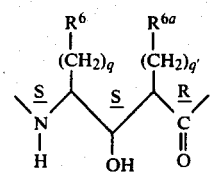   (10)

where q is 1 to 4; q' is 0 to 4; $R^6$ is $C_{3-6}$ alkyl; $C_{3-7}$ cycloalkyl; aryl; or $C_{3-7}$ cycloalkyl or aryl substituted with up to three members selected from the group consisting of $C_{1-4}$ alkyl, trifluoromethyl, hydroxy, $C_{1-4}$ alkoxy, and halo; and $R^{6a}$ is $C_{1-8}$ alkyl; $C_{2-8}$ alkyl substituted with one or two members independently selected from the group consisting of hydroxy, carboxy, carboxy ester or amide, amino, mono-, di-, or tri-$C_{1-4}$ alkylamino, and guanidyl; wherein said substitution occurs on the last 1 or 2 carbon atoms of the alkyl chain; aryl; $C_{3-7}$ cycloalkyl; or aryl or $C_{3-7}$ cycloalkyl substituted with up to three members selected from the group consisting of $C_{1-4}$ alkyl, trifluoromethyl, hydroxy, $C_{1-4}$ alkoxy, and halo;

J is

   (1)

where Y is —NH— or —O—; n is 0 to 5; and $R^7$ is hydrogen; hydroxy; $C_{1-4}$ alkyl; $C_{3-7}$ cycloalkyl; aryl; aryl substituted with up to five members independently selected from the group consisting of $C_{1-6}$ alkyl, trifluoromethyl, hydroxy, $C_{1-4}$ alkoxy, amino, mono- or di- $C_{1-4}$ alkylamino, and halo; amino; mono-, di-, or tri-$C_{1-4}$ alkylamino; guanidyl; heterocyclic; or heterocyclic substituted with up to five members independently selected from the group consisting of $C_{1-6}$ alkyl, hydroxy, trifluoromethyl, $C_{1-4}$ alkoxy, halo, aryl, aryl $C_{1-4}$ alkyl, amino, and mono- or di-$C_{1-4}$ alkylamino;

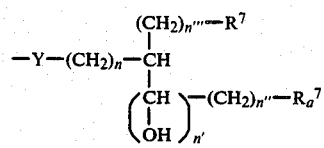   (2)

where Y is as defined above; n is 0 or 1; n' is 0 or 1; n'' is 1 to 4; n''' is 1 to 4; and $R^7$ and $R_a^7$ may be the same or different and have the same meaning as $R^7$ above and $R_a^7$ may additionally be

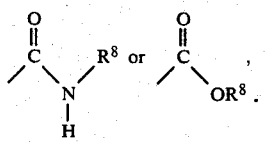

where $R^8$ is hydrogen or $C_{1-3}$ alkyl;

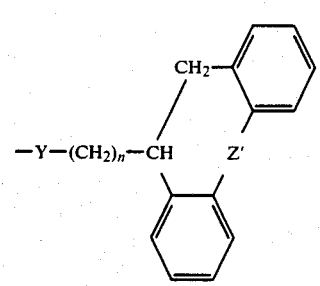   (3)

where Y is as defined above; n is 0 or 1; and Z' is (a) 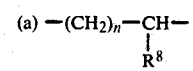

where n is 0 or 1; and $R^8$ is as defined above; or (b) 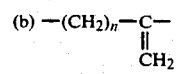

where n is 0 or 1;

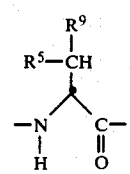   (4)

where $R^5$ is as defined above; and $R^9$ is hydrogen; $C_{1-4}$ alkyl; hydroxy; or $C_{3-7}$ cycloalkyl; or

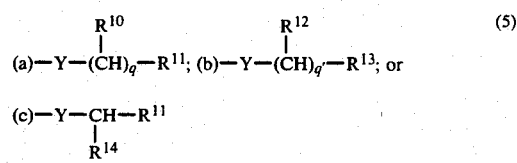   (5)

(c)—Y—CH—$R^{11}$
         |
         $R^{14}$ where Y is —NH— or —O—; q is 1–5; q' is 0–5; $R^{10}$ is hydrogen; hydroxy; N(R')$_2$ where R' may be the same or different and is hydrogen or $C_{1-4}$ alkyl; guanidyl; or N$^{\oplus}$(R')$_3$A$^{\ominus}$, where R' is as defined above, and A$^{\ominus}$ is a counterion; provided that at least one $R^{10}$ is not hydrogen; $R^{11}$ is $C_{1-4}$ alkyl; $C_{3-7}$ cycloalkyl; aryl; aryl substituted with up to three members independently selected from the group consisting of $C_{1-6}$ alkyl, tri-fluoromethyl, hydroxy, $C_{1-4}$ alkoxy, amino, mono- or di- $C_{1-4}$ alkylamino, amino $C_{1-4}$ alkyl, mono-, di-, or tri-$C_{1-4}$ alkylamino-$C_{1-4}$ alkyl, halo, carboxy, carboxy ester or amide, carboxy-$C_{1-4}$ alkoxy, carboxy-$C_{1-4}$-alkoxy ester or amide, α-aminocarboxy-$C_{1-4}$ alkyl, α-aminocarboxy-$C_{1-4}$ alkyl ester or amide, carboxy-$C_{1-4}$ alkyl, carboxy-$C_{1-4}$ alkyl ester or amide, guanidyl, and guanidyl-$C_{1-4}$ alkyl; carboxy, ester or amide; sulfo; heterocyclic; or heterocyclic substituted with up to five members independently selected from the group consisting of $C_{1-6}$ alkyl, hydroxy, trifluoromethyl, $C_{1-4}$ alkoxy, halo, aryl, aryl $C_{1-4}$ alkyl, amino, and mono- or di-$C_{1-4}$ alkylamino; $R^{12}$ is hydrogen; or carboxy, ester or amide; $R^{13}$ is carboxy, ester or amide; sulfo; or aryl substituted with up to three members selected from the group consisting of amino-$C_{1-4}$ alkyl, mono-, di-, or tri-$C_{1-4}$-alkylamino-$C_{1-4}$-alkyl, halo, carboxy, carboxy ester or amide, carboxy-$C_{1-4}$ alkoxy, carboxy-$C_{1-4}$ alkoxy ester or amide, α-aminocarboxy-$C_{1-4}$ alkyl, α-aminocarboxy-$C_{1-4}$ alkyl ester or amide, carboxy-$C_{1-4}$ alkyl, carboxy-$C_{1-4}$ alkyl ester or amide, guanidyl, and guanidyl-$C_{1-4}$ alkyl; and $R^{14}$ is carboxy, ester or amide; or (d) 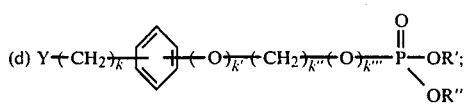

or (e) 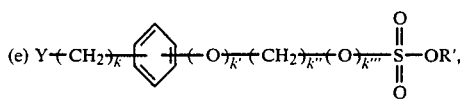

where Y is —NH— or —O—; k is 0-4; k' is 0 or 1; k" is 0-4; k'" is 0 or 1; R' is hydrogen or $C_{1-4}$ alkyl; and R" is hydrogen or $C_{1-4}$ alkyl;

L is absent; OR"; NHR"; or N(R")$_2$, where R" may be the same or different and is hydrogen or $C_{1-4}$alkyl; provided that, B and/or L are/is present only when J is

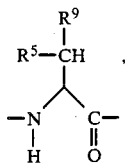

where $R^5$ and $R^9$ are as defined above;

$R^1$ is hydrogen; $C_{1-4}$alkyl; hydroxy $C_{1-4}$alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$alkyl; acyl $C_{2-4}$alkyl wherein the acyl is

and $R^9$ is as defined above; guanidyl $C_{2-3}$alkyl; or methylthiomethyl;

$R^4$ is hydrogen; or

where $R^9$ is as defined above; and $R^3$ is hydrogen; $C_{1-4}$alkyl; aryl; aryl $C_{1-4}$alkyl; aryl $C_{1-4}$alkyl or aryl substituted with up to three members selected from the group consisting of $C_{1-4}$alkyl, trifluoromethyl, hydroxy, $C_{1-4}$alkoxy, and halo; or indolyl; and wherein all of the asymmetric carbon atoms have an S configuration, except for those in the B and D substituents, which may have an S or R configuration, and the G group, which must have a 2R,4S,4S configuration; and a pharmaceutically acceptable salt thereof.

While both the S and R chiralities for asymmetric carbon atoms in the B substituent are included in the peptides of the present invention, preferred chiralities are indicated in the description which follows.

In the above definitions, the term "alkyl" is intended to include both branched and straight chain hydrocarbon groups having the indicated number of carbon atoms.

The term "halo" means fluoro, chloro, bromo and iodo.

The aryl substituent represents phenyl, and naphthyl.

The heterocyclic substituent recited above represents any 5- or 6-membered ring containing from one to three heteroatoms selected from the group consisting of nitrogen, oxygen, and sulfur; having various degrees of unsaturation; wherein the nitrogen and sulfur heteroatoms may optionally be oxidized; wherein the nitrogen heteroatom may optionally be quaternized; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Where the heterocyclic substituent itself is substituted, it is preferred that the substituent be aryl $C_{1-4}$alkyl.

The novel renin inhibitory peptides of the present invention may also be described in terms of common amino acid components and closely related analogs thereof, in accordance with the following formula:

$$A-B-B-D-E-Y-G-Z-J-B-L \qquad (II.)$$

The A, B, D, G, J and L components correspond to the same portions of Formula I.

The common amino acid components of Formula II are as follows:

A has the same meaning as above in Formula I;
B is Ala, Leu, Ser, Thr, Phe, Tyr, Trp, His, Lys, Orn, Arg, or Met;
D is Pro;
E is Ala, Leu, Phe, HomoPhe, BisHomoPhe, Tyr, HomoTyr, Trp, or HomoTrp;
Y is the same as B;
G has the same meaning as above in Formula I;
Z is Ala, Leu, Phe, Tyr, Trp, Ser, Gly, Val, Ile, or Thr;
J has the same meaning as above in Formula I; and
L has the same meaning as above in Formula I.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formula I and its definitions. Thus, the peptides of Formula II and its definitions represent preferred peptides of the present invention.

Heretofore, peptidyl inhibitors of renin have been described which contain statine and derivatives thereof as a dipeptide replacement for the 10 and 11 positions of the natural substrate. However, none of these statine derivatives contained any substituent at the 2-position, and it was not clear that the renin enzyme would permit any substituent at this position; or if it did, what the character and stereoconfiguration of such a substituent would be. We have now discovered that statine having a 2-substituent of the character described herein and having a 2R, 3S, 4S configuration, may form the basis of potent peptidyl inhibitors of human renin. This descovery resulted from our our investigation of the analogous enzyme, Rhizopus aspartic protease. Within its active site is a large, unfilled hydrophobic pocket directly adjacent to the C$_2$ of statine and near the catalytic site. Careful evaluation finally determined that an R configuration was required at this site.

Preferred inhibitory peptides of the present invention are the following:

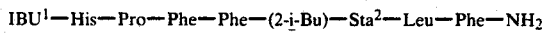

IBU$^1$—His—Pro—Phe—Phe—(2-i-Bu)—Sta$^2$—Leu—Phe—NH$_2$

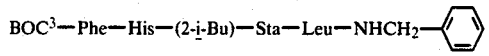

BOC$^3$—Phe—His—(2-i-Bu)—Sta—Leu—NHCH$_2$—⟨ ⟩

BOC—Phe—His—(2-i-Bu)—AHPPA$^4$—Leu—NHCH$_2$—⟨ ⟩

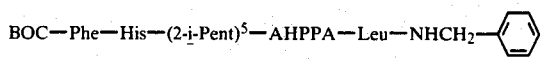

BOC—Phe—His—(2-i-Pent)$^5$—AHPPA—Leu—NHCH$_2$—⟨ ⟩

$^1$IBU = Iso-butyryl.
$^2$(2-i-Bu)—Sta = 4(S)—amino-3(S)—hydroxy-2(R)—iso-butyl-6-methylheptanoyl.
$^3$BOC = Tert-butyloxycarbonyl.
$^4$(2-i-Bu)—AHPPA = 4(S)—amino-3(S)—hydroxy-2(R)—iso-butyl-5-phenylpentanoyl.
$^5$(2-i-Pent) = 3-methylbutyl.

The inhibitory peptides of the present invention may be better appreciated in terms of substrate analogy from the following illustration of Formula I alongside the octapeptide sequence of a portion of the pig renin substrate, which renin cleaves between Leu$^{10}$ and Leu$^{11}$:

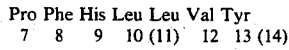

Pro Phe His Leu Leu Val Tyr
 7   8   9  10 (11) 12 13 (14)

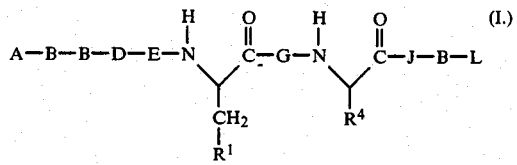

As can be seen, a unique aspect and essential feature of the present invention is the substitution of a 2-substituted statine component for the double amino acid sequence: Leu$^{10}$-Leu$^{11}$ in the endogenous pig renin substrate. It is believed that substitution of this component for both leucine amino acids rather than just one leucine results in an improved substrate analogy due to the greater linear extent of said component as compared to a single leucine component. Thus, the 2-substituted statine component more closely approximates Leu-Leu in linear extent, and thereby provides a better "fit" to the renin enzyme.

The inhibitory peptides of the present invention may also be better appreciated in terms of substrate analogy from the following illustration of Formula I alongside the octapeptide sequence of a portion of the human renin substrate, which renin cleaves between Leu$^{10}$ and Val$^{11}$:

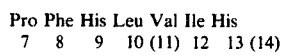

Pro Phe His Leu Val Ile His
 7   8   9  10 (11) 12 13 (14)

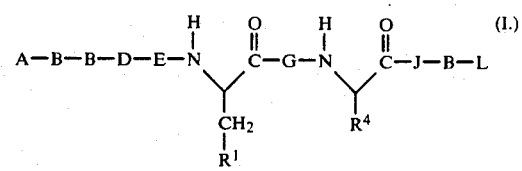

As can be seen, a unique aspect and essential feature of the present invention is the substitution of a 2-substituted statine component for the double amino acid sequence: Leu$^{10}$-Val$^{11}$ in the endogenous human renin substrate. It is believed that substitution of this component for both the leucine and valine amino acids rather than just the leucine results in an improved substrate analogy due to the greater linear extent of said component as compared to a single leucine component. Thus, the 2-substituted statine component more closely approximates Leu-Val in linear extent, and thereby provides a better "fit" to the human renin enzyme.

In the endogenous substrate it is also preferred to substitute Leu for Val$^{12}$ and Phe for Tyr$^{13}$ in order to enhance the inhibitory activity of the resulting peptide.

The Formula I compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The present invention is also directed to combinations of the novel renin-inhibitory peptides of Formula I with one or more antihypertensive agents selected from the group consisting of diuretics, α and/or β-adrenergic blocking agents, CNS-acting agents, adrenergic neuron blocking agents, vasodilators, angiotensin I converting enzyme inhibitors, and other antihypertensive agents.

For example, the compounds of this invention can be given in combination with such compounds or salt or other derivative forms thereof as:

Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate, sodium nitroprusside; spironolactone; ticrynafen; triamterene; trichlormethiazide;

α-Adrenergic Blocking Agents: dibenamine; phentolamine; phenoxybenzamine; prazosin; tolazoline;

β-Adrenergic Blocking Agents: atenolol; metoprolol; nadolol; propranolol; timolol;

((±)-2-[3-(tert-butylamino)-2-hydroxypropoxy]-2-furananilide) (ancarolol);
(2-acetyl-7-(2-hydroxy-3-isopropylaminopropoxy)benzofuran HCl) (befunolol);
((±)-1-(isopropylamino)-3-(p-(2-cyclopropylmethoxyethyl)-phenoxy)-2-propranol HCl) (betaxolol);
(1-[(3,4-dimethoxyphenethyl)amino]-3-(m-tolyloxy)-2-propanol HCl) (bevantolol);
((±)-1-(4-((2-isopropoxyethoxy)methyl)phenoxy)-3-isopropylamino-2-propanol)fumarate) (bisoprolol);
(4-(2-hydroxy-3-[4-(phenoxymethyl)-piperidino]-propoxy)-indole);
(carbazolyl-4-oxy-5,2-(2-methoxyphenoxy)-ethylamino-2-propanol);
(1-((1,1-dimethylethyl)amino)-3-((2-methyl-1H-indol-4-yl)oxy)-2-propanol benzoate) (bopindolol);
(1-(2-exobicyclo[2.2.1]-hept-2-ylphenoxy)-3-[(1-methylethyl)-amino]-2-propanol HCl) (bornaprolol);
(o-[2-hydroxy-3-[(2-indol-3-yl-1,1-dimethylethyl-)amino]propoxy]benzonitrile HCl) (bucindolol);
(α-[(tert.butylamino)methyl]-7-ethyl-2-benzofuranmethanol) (bufuralol);
(3-[3-acetyl-4-[3-(tert.butylamino)-2-hydroxypropyl]-phenyl]-1,1-diethylurea HCl) (celiprolol);
((±)-2-[2-[3-[(1,1-dimethylethyl)amino]-2-hydroxypropoxy]phenoxy]-N-methylacetamide HCl) (cetamolol);
(2-benzimidazolyl-phenyl(2-isopropylaminopropanol));
((±)-3'-acetyl-4'-(2-hydroxy-3-isopropylaminopropoxy)acetanilide HCl) (diacetolol);
(methyl-4-[2-hydroxy-3-[(1-methylethyl)aminopropoxy]]-benzenepropanoate HCl) (esmolol);
(erythro-DL-1-(7-methylindan-4-yloxy)-3-isopropylaminobutan-2-ol);
(1-(tert.butylamino)-3-[O-(2-propynyloxy)phenoxy]-2-propanol (pargolol);
(1-(tert.butylamino)-3-[o-(6-hydrazino-3-pyridazinyl)-phenoxy]-2-propanol diHCl) (prizidilol);
((−)-2-hydroxy-5-[(R)-1-hydroxy-2-[(R)-(1-methyl-3-phenylpropyl)amino]ethyl]benzamide);
(4-hydroxy-9-[2-hydroxy-3-(isopropylamino)-propoxy]-7-methyl-5H-furo[3,2-g][1]-benzopyran-5-one) (iprocrolol);
((−)-5-(tert.butylamino)-2-hydroxypropoxy]-3,4-dihydro-1-(2H)-naphthalenone HCl) (levobunolol);
(4-(2-hydroxy-3-isopropylamino-propoxy)-1,2-benzisothiazole HCl);
(4-[3-(tert.butylamino)-2-hydroxypropoxy]-N-methylisocarbostyril HCl);
((±)-N-2-[4-(2-hydroxy-3-isopropyl aminopropoxy)-phenyl]ethyl-N'-isopropylurea) (pafenolol);
(3-[[(2-trifluoroacetamido)ethyl]amino]-1-phenoxypropan-2-ol);
(N-(3-(o-chlorophenoxy)-2-hydroxypropyl)-N'-(4'-chloro-2,3-dihydro-3-oxo-5-pyridazinyl)ethylenediamine);
((±)-N-[3-acetyl-4-[2-hydroxy-3-[(1-methylethyl-)amino]propoxy]phenyl]butanamide) (acebutolo);
((±)-4'-[3-(tert-butylamino)-2-hydroxypropoxy]spiro[cyclohexane-1,2'-indan]-1'-one) (spirendolol);
(7-[3-[[2-hydroxy-3-[(2-methylindol-4-yl)oxy]propyl]-amino]butyl]thiophylline) (teoprolol);
((±)-1-tert.butylamino-3-(thiochroman-8-yloxy)-2-propanol) (tertatolol);
((±)-1-tert.butylamino-3-(2,3-xylyloxy)-2-propanol HCl) (xibenolol);
(8-[3-(tert-butylamino)-2-hydroxypropoxy]-5-methylcoumarin) (bucumolol);
(2-(3-(tert.butylamino)-2-hydroxy-propoxy)benzonitrile HCl) (bunitrolol);
((±)-2'-[3-(tert-butylamino)-2-hydroxypropoxy-5'-fluorobutyrophenone] (butofilolol);
(1-(carbazol-4-yloxy)-3-(isopropylamino)-2-propanol) (carazolol);
(5-(3-tert.butylamino-2-hydroxy)propoxy-3,4-dihydrocarbostyril HCl) (carteolol);
(1-(tert.butylamino)-3-(2,5-dichlorophenoxy)-2-propanol) (cloranolol);
(1-(inden-4(or 7)-yloxy)-3-(isopropylamino)-2-propanol HCl) (indenolol);
(1-isopropylamino-3-[(2-methylindol-4-yl)oxy]-2-propanol) (mepindolol);
(1-(4-acetoxy-2,3,5-trimethylphenoxy)-3-isopropylaminopropan-2-ol) (metipranolol);
(1-(isopropylamino)-3-(o-mehoxyphenoxy)-3-[(1-methylethyl)amino]-2-propanol) (moprolol);
((1-tert.butylamino)-3-[(5,6,7,8-tetrahydro-cis-6,7-dihydroxy-1-naphthyl)oxy]-2-propanol) (nadolol);
((S)-1-(2-cyclopentylphenoxy)-3-[(1,1-dimethylethyl-)amino]-2-propanol sulfate (2:1)) (penbutolol);
(4'-[1-hydroxy-2-(amino)ethyl]methanesulfonanilide) (sotalol);
(2-methyl-3-[4-(2-hydroxy-3-tert.butylaminopropoxy)-phenyl]-7-methoxy-isoquinolin-1-(2H)-one);
(1-(4-(2-(4-fluorophenyloxy)ethoxy)phenoxy)-3-isopropylamino-2-propanol HCl);
((−)-p-[3-[(3,4-dimethoxyphenethyl)amino]-2-hydroxypropoxy]-β-methylcinnamonitrile) (pacrinolol);
((±)-2-(3'-tert.butylamino-2'-hydroxypropylthio)-4-(5'-carbamoyl-2'-thienyl)thiazole HCl) (arotinolol);
((±)-1-[p-[2-cyclopropylmethoxy)ethoxy]phenoxy]-3-(isopropylamino)-2-propanol) (cicloprolol);
((±)-1-[(3-chloro-2-methylindol-4-yl)oxy]-3-[(2-phenoxyethyl)amino]-2-propanol) (indopanolol);
((±) -6-[[2-[[3-(p-butoxyphenoxy)-2-hyroxypropyl]amino]ethyl]amino]-1,3-dimethyluracil) (pirepolol);
(4-(cyclohexylamino)-1-(1-naphtholenyloxy)-2-butanol);
(1-phenyl-3-[2-[3-(2-cyanophenoxy)-2-hydroxypropyl]aminoethyl]hydantoin HCl);
(3,4-dihydro-8-(2-hydroxy-3-isopropylaminopropoxy)-3-nitroxy-2H-1-benzopyran) (nipradolol);

α and β-Adrenergic Blocking Agents:
((±)-1-tert-butylamino-3-[o-[2-(3-methyl-5-isoxazolyl)vinyl]phenoxy]-2-propanol) (isoxaprolol);
(1-isopropylamino-3-(4-(2-nitroxyethoxy)phenoxy)-2-propanol HCl);

(4-hydroxy-α-[[3-(4-methoxyphenyl)-1-methylpropyl]-aminomethyl]-3-(methylsulfinyl)-benzmethanol HCl) (sulfinalol);

(5-[1-hydroxy-2-[[2-(o-methoxyphenoxy)ethyl]amino]-ethyl]-2-methylbenzenesulfonamide HCl);

(5-[1-hydroxy-2-[(1-methyl-3-phenylpropyl)amino]ethyl]-salicylamide HCl) (labetalol);

(1-((3-chloro-2-methyl-1H-indol-4-yl)oxy)-3-((2-phenoxyethyl)amino)-2-propanol-hydrogenmalonate) (ifendolol);

(4-(2-hydroxy-3-[(1-methyl-3-phenylpropyl)amino]-propoxy)benzeneacetamide);

(1-[3[[3-(1-naphthoxy)-2-hydroxypropyl]-amino]-3,3-dimethyl-propyl]-2-benzimidazolinone);

(3-(1-(2-hydroxy-2-(4-chlorophenylethyl))-4-piperidyl)-3,4-dihydroxy)quinoxolin-2(1H)-one);

CNS-Acting Agents: clonidine; methyldopa;

Adrenergic Neuron Blocking Agents: guanethidine; reserpine and other rauwolfia alkaloids such as rescinnamine;

Vasodilators: diazoxide; hydralazine; minoxidil;

Angiotensin I Converting Enzyme Inhibitors:

1-(3-mercapto-2-methyl-1-oxopropyl)-L-proline (captopril);

(1-(4-ethoxycarbonyl-2,4(R,R)-dimethylbutanoyl)-indoline-2(S)-carboxylic acid);

(2-[2-[[1-(ethoxycarbonyl)-3-phenyl-propyl]amino]-1-oxopropyl]-1,2,3,4-tetrahydro-3-isoquinoline carboxylic acid);

((S)-1-[2-[[1-(ethoxycarbonyl)-3-phenylpropyl]amino]-1-oxopropyl]octahydro-1H-indole-2-carboxylic acid HCl);

(N-cyclopentyl-N-(3-(2,2-dimethyl-1-oxopropyl)thiol-2-methyl-1-oxopropyl)glycine) (pivalopril);

((2R,4R)-2-(2-hydroxyphenyl)-3-(3-mercaptopropionyl)-4-thiazolidinecarboxylic acid;

(1-(N-[1(S)-ethoxycarbonyl-3-phenylpropyl]-(S)-alanyl)-cis,syn-octahydroindol-2(S)-carboxylic acid HCl);

((-)-(S)-1-[(S)-3-mercapto-2-methyl-1-oxopropyl]-indoline-2-carboxylic acid);

([1(S),4S]-1-[3-(benzoylthio)-2-methyl-1-oxopropyl]-4-phenylthio-L-proline;

(3-([1-ethoxycarbonyl-3-phenyl-(1S)-propyl]amino)-2,3,4,5-tetrahydro-2-oxo-1-(3S)-benzazepine-1-acetic acid HCl);

(N-(2-benzyl-3-mercaptopropanoyl)-S-ethyl-L-cysteine) and the S-methyl analogue;

(N-(1(S)-ethoxycarbonyl-3-phenylpropyl)-L-alanyl-L-proline maleate) (enalapril);

N-[1-(S)-carboxy-3-phenylpropyl]-L-alanyl-1-proline;

N²-[1-(S)-carboxy-3-phenylpropyl]-L-lysyl-L-proline (lysinopril);

Other Antihypertensive Agents: aminophylline; cryptenamine acetates and tannates; deserpidine; meremethoxylline procaine, pargyline; trimethaphan camsylate;

and the like, as well as admixture and combinations thereof.

Typically, the individual daily dosages for these combinations can range from about one-fifth of the minimally recommended clinical dosages to the maximum recommended levels for the entities when they are given singly. Coadministration is most readily accomplished by combining the active ingredients into a suitable unit dosage form containing the proper dosages of each. Other methods of coadministration are, or course, possible.

The novel peptides of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection of infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 0.1 to 4.0 grams per day are useful in the treatment of the above indicated conditions. For example, renin-associated hypertension and hyperaldosteronism are effectively treated by the administration of from 1.0 to 50 milligrams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

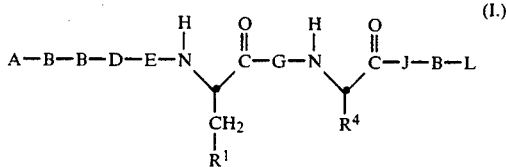

(I.)

wherein A, B, D, E, $R^1$, G, $R^4$, J, and L have the same meaning as recited further above for Formula I; wherein all of the asymmetric carbon atoms have an S configuration, except for those in the B and D substituents, which may have an S or R configuration, and the G group, which must have a 2R,3S,4S configuration; and a pharmaceutically acceptable salt thereof.

Also, in accordance with the present invention there is still further provided a method of treating renin-associated hypertension and hyperaldosteronism, comprising administering to a patient in need of such treatment, a therapeutically effective amount of a peptide of the formula:

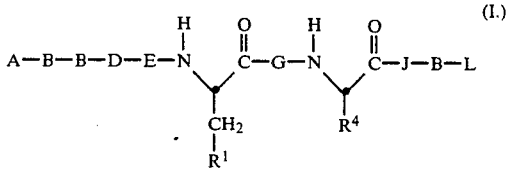

(I.)

wherein A, B, D, E, $R^1$, G, $R^4$, J, and L have the same meaning as recited further above for Formula I; wherein all of the asymmetric carbon atoms have an S configuration, except for those in the B and D substituents, which may have an S or R configuration, and the G group, which must have a 2R,3S,4S configuration; and a pharmaceutically acceptable salt thereof.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the in vivo method, a novel peptide of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids, which will be described in more detail below.

A general method of preparation may be described in the following terms:

A method of preparing a peptide of Formula I, said peptide being comprised of from two to eight amino acids identified as I through VII, amino acid (AA) I being at the C-terminus of said peptide, to which the substituent L is attached, and amino acid (AA) VIII being at the N-terminus of said peptide, to which substituent A is attached, but also including the 2-substituted statine component G, comprising the steps of:

(A) treating the desired ester or amide of the C-terminus amino acid (AA I) with the next adjacent amino acid (AA II) of said peptide, or 2-substituted statine component G, the amino group of said amino acid or component being protected by a protecting group, in the presence of a condensing agent, whereby a dipeptide of the two amino acids (AA I and II) or component G is formed;

(B) deprotecting the dipeptide formed in Step (A) by removing the protecting group from the amino group of AA II or component G;

(C) treating the dipeptide of AA I and AA II or component G with AA III, the amino group of which is protected by a protecting group, in the presence of a condensing agent, whereby a tripeptide of AA I, AA II and AA III is formed;

(D) deprotecting the tripeptide formed in Step (C) by removing the protecting group from the amino group of AA III, to give the peptide of Formula I wherein A is hydrogen; the Steps (C) and (D) also optionally being carried out so as to introduce the 2-substituted statine component G;

(E) treating the tripeptide formed in Step (D) where an ester of AA I is employed with hydrazine to give the corresponding hydrazide, followed by treatment of said hydrazide with acidic nitrite to give the corresponding acyl azide, followed by treatment of said acyl azide with the appropriate amine compound to give the desired J substituent which is not an amino acid, in the peptide of Formula I; and optionally (F) treating the tripeptide formed in Step (E) with

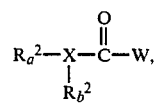

where X, $R_a^2$, and $R_b^2$, are as defined above and W is an acid halide, anhydride, or other carbonyl activating group, to give the peptide of Formula I wherein A is other than hydrogen; and optionally (G) forming a tetrapeptide up to an octapeptide of AA I, through AA VIII, by repeating the procedure of Step (C) using protected AA IV through protected AA VIII;

(H) deprotecting the tetrapeptide through octapeptide formed in Step (G) to give the peptide of Formula I wherein A is hydrogen; and optionally (I) treating the tetrapeptide through octapeptide formed in Step (H) with

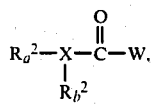

where X, $R_a{}^2$, and $R_b{}^2$ are as defined above and W is an acid halide, anhydride, or other carboxyl activating group, to give the peptide of Formula I wherein A is other than hydrogen;

said method also comprising, where necessary, protection of sidechain substituents of the component amino acids AA I through AA V, with deprotection being carried out as a final step; said method also comprising any combination of the steps set out above, whereby the amino acids I through VIII and substituents A, B, D, E, G, J, and L are assembled in any desired order to prepare the peptide of Formula I; and said method also comprising employment of the steps set out above in a solid phase sequential synthesis, whereby in the initial step the carboxyl group of the selected amino acid is bound to a synthetic resin substrate while the amino group of said amino acid is protected, followed by removal of the protecting group, the succeeding steps being as set out above, the peptide as it is assembled being attached to said synthetic resin substrate; followed by a step of removing the peptide of Formula I from said synthetic resin substrate: (a) by strong acid cleavage to give L=OH; (b) by transesterification with a $C_{1-4}$ alkanol to give L=O—$C_{1-4}$ alkyl (followed by hydrolysis to give L=OH); or (c) by ammonolysis with $NH_2R''$ where $R''$ is hydrogen or $C_{1-4}$ alkyl; said removal steps also optionally being carried out as treatments where solid phase sequential synthesis is not carried out, to give the same L substituent endings; and after removal of the peptide of Formula I from said synthetic resin substrate by transesterification to form the ester thereof as recited above, optionally the step of teating said ester thereof in accordance with the procedures described in Step (E) above to give the desired J substituent in the peptide of Formula I; removal of sidechain protecting groups being accomplished either before or after removal of the peptide of Formula I from said synthetic resin substrate.

Preparation of the peptides of Formula I having the desired J substituent, as described above in Step (E), may be illustrated as follows for the particular case where J×benzylamide (and PEP represents the remaining portion of the peptide of Formula I):

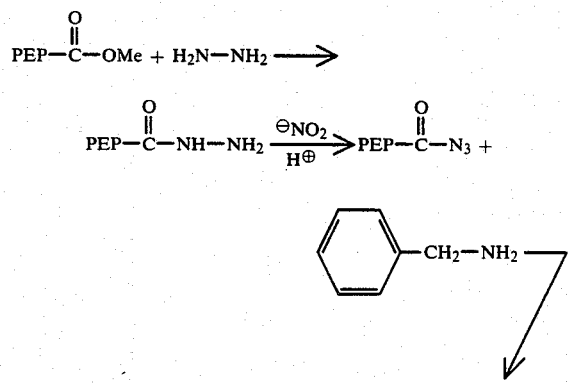

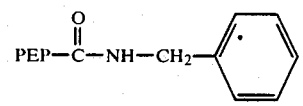

An efficient method of preparing the 2-substituted statine component G in the required 2R,3S,4S configuration begins with the preparation of protected phenylalanine aldehyde 1 in three steps beginning from phenylalanine, illustrated as follows:

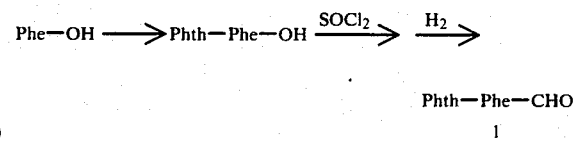

This aldehyde 1 can then be reacted with the ketone silylacetal 2 in a titanium mediated aldol condensation to afford an approximately 1:1 mixture of 3a and 3b, illustrated as follows:

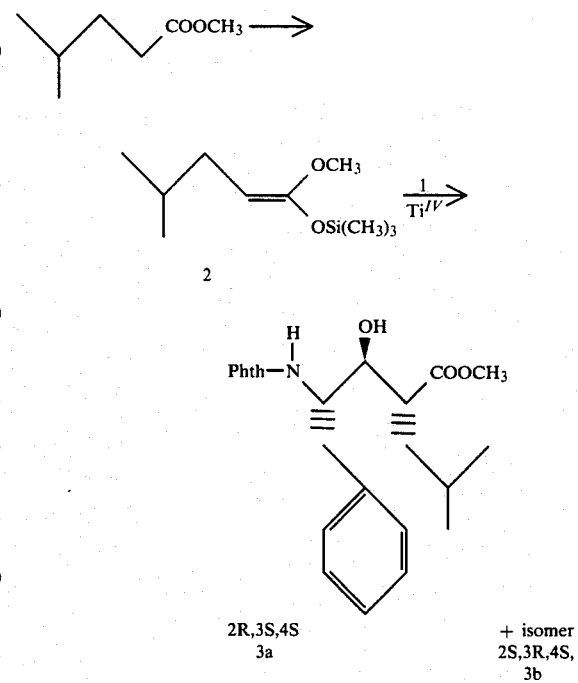

Diasterioselectivity favors by 95% formation of the 3a isomer, and the two diastereomers are thus readily separated by chromatography.

The configurations of the chiral centers can be established as follows: treatment of the phthalimido methyl esters 3a and 3b with excess hydrazine gives the respective amino acyl hydrazides 4a and 4b, which are then converted in a two step/one pot procedure to the corresponding lactams 5a and 5b, to which stereochemical assignments can be made based on PMR analysis. These reactions may be illustrated as follows:

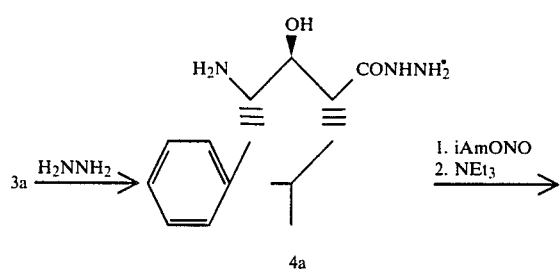

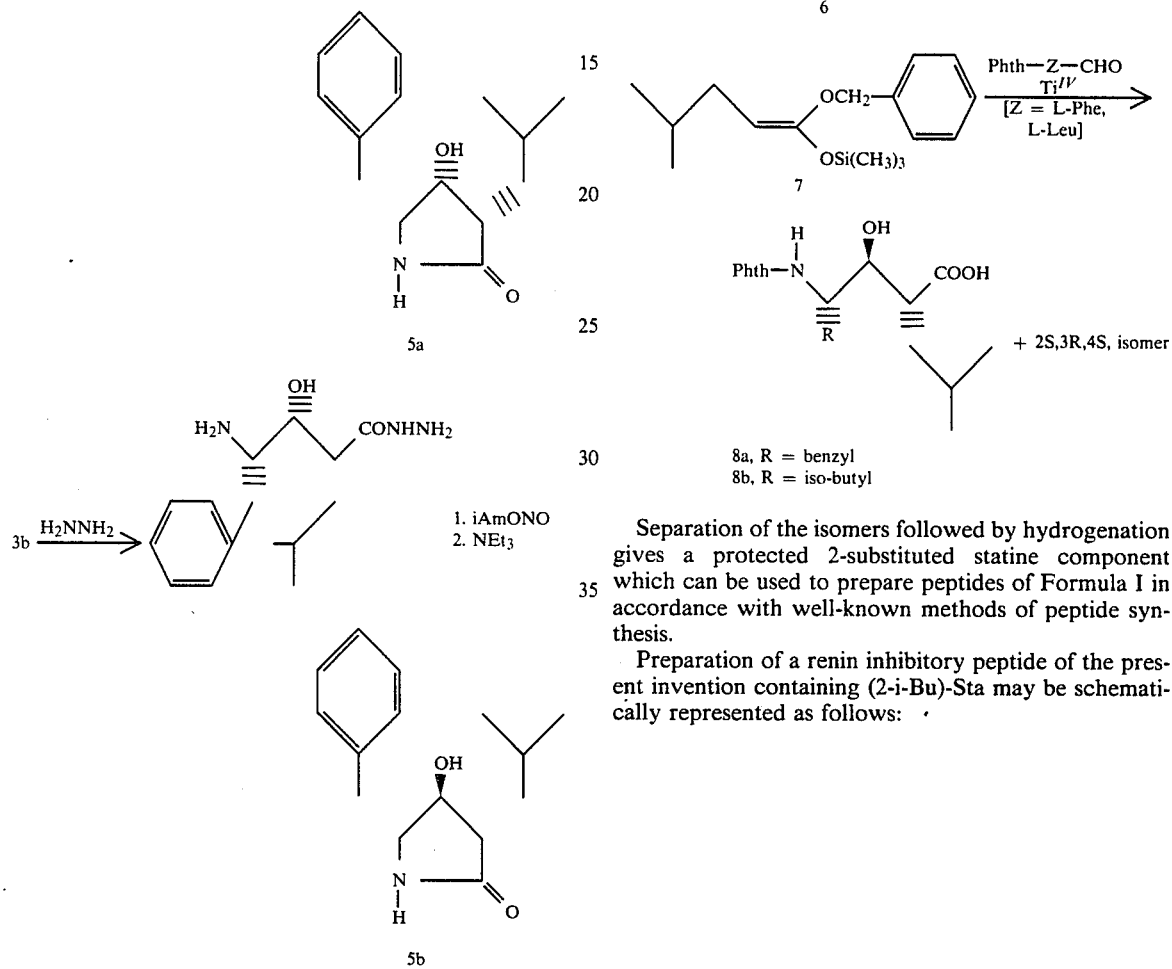

Alternatively, the benzyl ester 6, rather than the methyl ester, may be used to form the ketone silylacetal 7, which can then be reacted with phthalyl phenylalanine aldehyde and phthalyl leucine aldehyde, for example, to give 8a and 8b, illustrated as follows:

Separation of the isomers followed by hydrogenation gives a protected 2-substituted statine component which can be used to prepare peptides of Formula I in accordance with well-known methods of peptide synthesis.

Preparation of a renin inhibitory peptide of the present invention containing (2-i-Bu)-Sta may be schematically represented as follows:

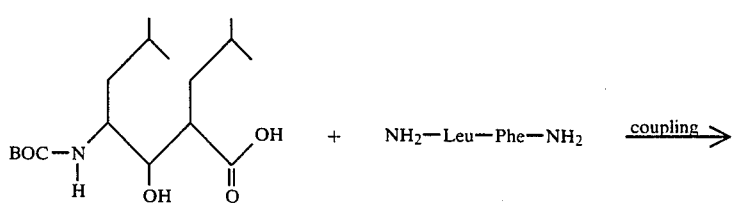

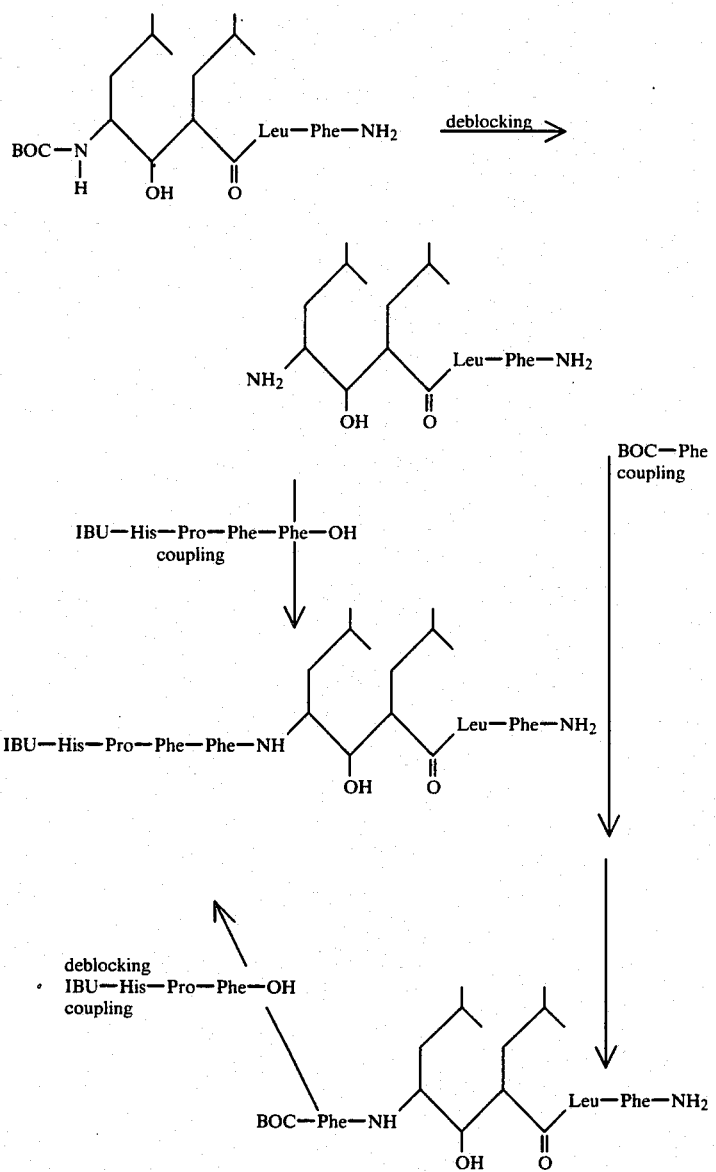

The novel inhibitory peptides of the present invention are prepared by using the solid phase sequential synthesis technique.

In the following description several abbreviated designations are used for the amino acid components, certain preferred protecting groups, reagents and solvents. The meanings of such abbreviated designations are given below in Table I.

TABLE I

| Abbreviated Designation | Amino Acid |
|---|---|
| Ala | L-alanine |
| Arg | L-arginine |
| Gly | L-glycine |
| His | D or L-histidine |
| Ile | L-isoleucine |
| Leu | L-leucine |
| Lys | L-lysine |
| Met | L-methionine |
| Orn | L-ornithine |
| Phe | L-phenylalanine |

TABLE I-continued

| Abbreviated Designation | |
|---|---|
| Ser | L-serine |
| Sar (N—methylglycine) | L-sarcosine |
| Thr | L-threonine |
| Trp | L-tryptophan |
| Tyr | L-tyrosine |
| Val | L-valine |
| Protecting Groups | |
| BOC | tert-butyloxycarbonyl |
| CBZ | benzyloxycarbonyl |
| DNP | dinitrophenyl |
| OMe | methyl ester |
| Activating Groups | |
| HBT | 1-hydroxybenzotriazole |
| Condensing Agents | |
| DCCI | dicyclohexylcarbodiimide |
| DPPA | diphenylphosphorylazide |

TABLE I-continued

| Abbreviated Designation | |
|---|---|
| | Reagents |
| TEA | triethylamine |
| TFA | trifluoroacetic acid |
| | Solvents |
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptides of the present invention by the solid phase technique is conducted in a stepwise manner on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONP ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyoxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the -amino group of Lys can be protected by the INOC group or the 2-chlorobenzyloxycarbonyl (2-Cl-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptides of the present invention is illustrated in the following examples, which however, are not intended to be any limitation of the present invention.

EXAMPLE 1 tert-Butyloxycarbonyl-L-phenylalanyl-L-histidyl-4(S)-amino-3(S)-hydroxy-2(R)-iso-butyl-5-phenylpentanoyl-L-leucyl-benzylamide

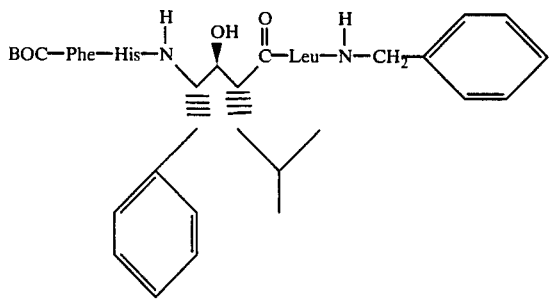

Step A:
N-phthalyl-O-benzyl-4(S)-amino-3(S)-hydroxy-2-(R)-iso-butyl-5-phenylpentanoic acid Phthaloyl-S-leucinal (1.7 g, 6.1 mmole), prepared according to the method described in Foye, *J. Amer. Pharm. Assoc.* 45: 742–744, 1956, was dissolved in 30 ml. of dry methylene chloride under an inert atmosphere; and the resulting solution was cooled to −78° C., stirred rapidly, and treated dropwise with 0.67 ml (6.1 mmole) of titanium tetrachloride. The orange-brown heterogeneous reaction mixture was stirred for 10 minutes more and then 1-benzyloxy-4-methyl-1-trimethylsilyloxypentene (2.0 g, 7.18 mmole) was added neat at −78° C. The reaction mixture became homogeneous within 10 minutes. Stirring was continued for 30 minutes at −78° C., then the reaction mixture was warmed to room temperature over 1 hour and quenched with brine. The reaction mixture was partitioned between ether/water; the organic phase was separated and washed with saturated sodium bicarbonate solution and brine, then dried with magnesium sulfate and rotoevaporated. Crude product (3.05 g) as an oil was obtained. Diasteriomerically pure [2R, 3S, 4S] product was obtained by column chromatography on silica gel (hexane/ethyl acetate, 3:1, v/v) in 49% overall yield. Spectral data ws consistent with the assigned structure.

Step B:
N-phthalyl-4(S)-amino-3(S)-hydroxy-2(R)-iso-butyl-5-phenylpentanoic acid The product of Step A (1.4 g, 2.88 mmole) was dissolved in 40 ml of absolute ethanol, treated with 200 mg of 10% palladium on carbon, and hydrogenated on a Parr apparatus at 55 psi for 8 hours. The reaction mixture was filtered through diatomaceous earth and concentrated to give 1.04 g of the title compound (91% yield). Spectral data was consistent with the assigned structure.

Step C:
N-phthalyl-4(S)-amino-3(S)-hydroxy-2(R)-iso-butyl-5-phenylpentanoyl-L-leucylbenzylamide The product of Step B (430 mg, 1.08 mmole), L-leucyl benzylamide HCl (333 mg, 1.30 mmole) ethyldimethylaminoethylcarbodiimide HCl (249 mg, 1.30 mmole), and N-hydroxy benzotriazole (130 mmole) were combined at room temperature with 15 ml of dry dimethylformamide. The pH of the resulting reaction mixture was adjusted to 8.5 with diisopropyl ethylamine, and the reaction mixture was stirred with the exclusion of moisture for 4 hours. The solvent was removed under reduced pressure and the residue was partitioned between ethyl acetate and brine. The organic phase was washed in succession with 10% citric acid solution (3×15 ml), saturated sodium bicarbonate solution (3×15 ml), and brine. Rotoevaporation of the organic phase previously dried over magnesium sulfate gave 720 mg of the title compound. Spectral data was in accord with the assigned structure.

Step D:
tert-Butyloxycarbonyl-L-Histidyl-2,4-dinitrophenyloxy-4(S)-amino-3(S)-hydroxy-2(R)-iso-butyl-5-phenylpentanoyl-L-leucyl-benzylamide The product of Step C (600 mg, 0.71 mmole) was dissolved in 25 ml of dry ethyl acetate. The resulting solution was cooled to 0° C. and treated with a stream of hydrogen chloride gas for 1 hour. Solvent and excess hydrogen chloride were removed under reduced pressure and the crude amine-HCl salt was dried in vacuo. BOC-L-phenylalanine (75 mg, 0.285 mmole) was then coupled to the amine-HCl salt (200 mg, 0.26 mmole) using dicyclohexylcarbodiimide (59 mg, 0.285 mmole), N-hydroxy benzoytriazole (38 mg, 0.285 mmole, and triethylamine (40 μl, 0.285 mmole) in 8 ml of dry dichloromethane. Extraction in accordance with the procedures described above in Step C gave 210 mg of th title compound, which was taken to the following step without further purification.

Step E:
tert-Butyloxycarbonyl-L-phenylalanyl-L-histidyl-4(S)-amino-3(S)-hydroxy-2(R)-iso-butyl-5-phenylpentanoyl-L-leucyl-benzylamide The product of Step D (120 mg, 0.117 mmole) was dissolved in 3 ml of dry dimethylformamide and treated with 6 mg (0.06 mmole) of triethylamine and 0.5 ml of thiophenol. The reaction mixture was protected from moisture and allowed to stand at room temperature for 2 hours. The solvent and excess reagent were removed under reduced pressure and the residual solid was applied directly to four pre-coated silica gel 60F-254 (0.5 mm×20×20 cm) plates using chloroform-methanol-ammonia as eluent (95:5:0.5 v/v). Analytically pure product (37 mg) was obtained whose spectral data was in accord with the assigned structure.

EXAMPLES 2–4

Following the procedures described above in Example 1, other peptidyl renin inhibitors of the present invention were prepared and are set out in the following table:

| Exp. No. | Peptide |
|---|---|
| 2 | IBU—His—Pro—Phe—Phe—(2-i-Bu)—Sta—Leu—Phe—NH$_2$ |
| 3 | BOC—Phe—His—(2-i-Bu)—Sta—Leu—NHCH$_2$— |
| 4 | BOC—Phe—His—(2-i-Pent)—AHPPA—Leu—NHCH$_2$— |

EXAMPLE 5

Renin Inhibition

Assays were carried out in order to determine the inhibitory potency of the peptides of the present invention. One assay measured the inhibition of hog kidney renin, and was in accordance with the procedure described in Rich et al., *J. Med. Chem.* 23: 27, 1980, except that a pH of 7.3 was used. Another assay measured the inhibition of human kidney renin purified as described in Bangham, D. R., Robertson, I., Robinson, J. I. S., Robinson, C. J., and Tree, M., *Clinical Science and Molecular Medicine*, 48 (Supp. 2): 136s–159s (1975), and further purified by affinity chromatography on pepstatin-aminohexyl-Sepharase as described in Poe, M., Wu., J. K., Florance, J. R., Radkey, J. A., Bennett, C. D., and Hoogsteen, K., *J. Biol. Chem.* 258: 2209–2216 (1983). The assay was also in accordance with Poe et al. cited above. Further assays measured human plasma renin and dog plasma renin in accordance with procedures described in Boger et al., *Nature*, 303: 81–84 (1983).

Results expressed as K$_I$ values refer to the dissociation constant of the inhibited enzyme inhibitor complex. This K$_I$ value was obatined as described above. Pepstatin was used as an active control. The results are set out in the table below.

| | Renin Inhibition | | | |
|---|---|---|---|---|
| Peptide | Hog Kidney I$_{50}$ (nM) | Human Kidney K$_I$ (nM) | Human Plasma I$_{50}$ (nM) | Dog Plasma I$_{50}$ (nM) |
| BOC—Phe—His—(2-i-Bu)—AHPPA—Leu—NHCH$_2$— | 90% I 10$^{-9}$ | 9.3 | 8.2 | 3.5 |
| IBU—His—Pro—Phe—Phe—(2-i-Bu)—Sta—Leu—Phe—NH$_2$ | 22 | .77 | 33 | 27 |
| BOC—Phe—His—(2-i-Bu)—Sta—Leu—NHCH$_2$— | — | 10 | 26% I 10$^{-6}$ | 0% I 10$^{-6}$ |
| BOC—Phe—His—(2-i-Pent)—AHPPA—Leu—NHCH$_2$— | 72% I 10$^{-9}$ | 4.4 | 65 | 6.2 |

What is claimed is:
1. a peptide of the formula:

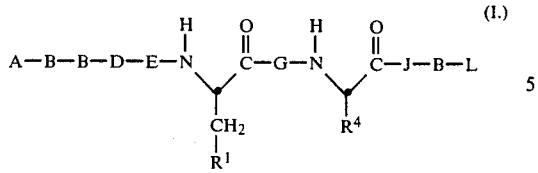 (I.)

wherein:
A is hydrogen; or

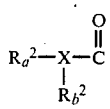

where X is —O—; —O—CH—; —CH—O—; —CH—; —NH—CH—; or —S—CH— and $R_a^2$ and $R_b^2$ may be the same or different and are hydrogen; W—$(CH_2)_n$— or W—$(CH_2)_m$—CH=CH—$(CH_2)_p$, where W is hydrogen; $C_{1-4}$alkyl; phenyl; naphthyl; $C_{3-7}$cycloalkyl; or mono- or disubstituted phenyl, naphthyl or $C_{3-7}$cycloalkyl wherein the substituent(s) is/are independently selected from the group consisting of $C_{1-8}$alkyl, trifluoromethyl, hydroxy, $C_{1-4}$alkoxy, and halo; n is 0 to 5; m is 0 to 2; and p is 0 to 2; except that where X is —O—, only one of $R_a^2$ or $R_b^2$ is present;

B is absent; glycyl; sarcosyl; or

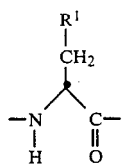

where $R^1$ is as defined further below;

D is absent; or

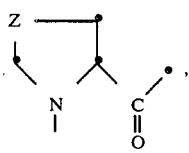

where Z is —$(CH_2)_l$— and l is 1 or 2; or —S—;

E is absent; or

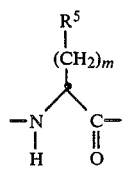

where m is 1 to 4; and $R^5$ is hydrogen; $C_{1-4}$ alkyl; indolyl; phenyl; naphthyl; phenyl-$C_1$-$C_4$-alkyl; naphthyl-$C_1$-$C_4$-alkyl; or mono- or disubstituted phenyl, naphthyl, phenyl-$C_1$-$C_4$-alkyl or naphthyl-$C_1$-$C_4$-alkyl, wherein the substituent(s) is/are selected from the group consisting of $C_{1-4}$ alkyl, trifluoromethyl, hydroxy, $C_{1-4}$ alkoxy, and halo;

G is

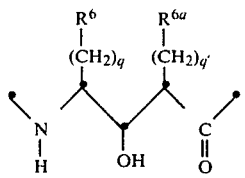

where q is 1 to 4; q' is 0 to 4; $R^6$ is $C_{3-6}$ alkyl; $C_{3-7}$ cycloalkyl; phenyl; naphthyl; or mono- or disubstituted phenyl, naphthyl or $C_{3-7}$cycloalkyl, wherein the substituent(s) is/are selected from the group consisting of $C_{1-4}$alkyl, trifluoromethyl, hydroxy, $C_{1-4}$alkoxy, and halo; and $R^{6a}$ is $C_{1-8}$alkyl; $C_{2-8}$alkyl substituted with one or two members independently selected from the group consisting of hydroxy, carboxy, carboxy ester or amide, amino, mono-, di-, or tri-$C_{1-4}$alkylamino, and guanidyl; wherein said substitution occurs on the last 1 or 2 carbon atoms of the alkyl chain; phenyl; naphthyl; $C_{3-7}$cycloalkyl; or mono- or disubstituted phenyl, naphthyl or $C_{3-7}$cycloalkyl, wherein the substituent(s) is/are selected from the group consisting of $C_{1-4}$alkyl, trifluoromethyl, hydroxy, $C_{1-4}$alkoxy, and halo;

J is $$-Y-(CH_2)_n-R^7 \quad (1)$$

where Y is —NH— or —O—; n is 0 to 5; and $R^7$ is hydrogen; hydroxy; $C_{1-4}$alkyl; $C_{3-7}$cycloalkyl; unsubstituted or mono- or disubstituted phenyl or naphthyl, wherein the substituent(s) is/are independently selected from the group consisting of $C_{1-6}$alkyl, trifluoromethyl, hydroxy, $C_{1-4}$alkoxy, amino, mono- or di-$C_{1-4}$alkylamino, and halo; amino; mono-, di-, or tri-$C_{1-4}$alkylamino; guanidyl; or an unsubstituted or mono- or disubstituted heterocycle, representing a 5- or 6-membered ring or benzofused 5- or 6-membered ring comprising one or two heteroatoms independently selected from N, O and S, where the substituent(s) is/are independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

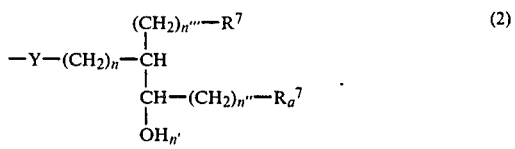 (2)

where Y is as defined above; n is 0 or 1; N' is 0 or 1; n" is 1 to 4; n'" is 1 to 4; and $R^7$ and $R_a^7$ may be the same or different and have the same meaning as $R^7$ above and $R_a^7$ may additionally be

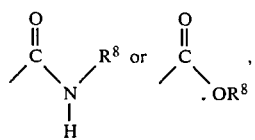

where $R^8$ is hydrogen or $C_{1-3}$alkyl;

$$Y-(CH_2)_n-CH\begin{matrix}CH_2-\phantom{x}\\ \phantom{x}\\ Z'\end{matrix} \quad (3)$$

where Y is as defined above; n is 0 or 1; and Z' is (a) $-(CH_2)_n-\underset{R^8}{\overset{|}{CH}}-$ where n is 0 or 1; and $R^8$ is as defined above; or (b) $-(CH_2)_n-\underset{CH_2}{\overset{\|}{C}}-$ where n is 0 or 1;

$$\begin{matrix} & R^9 & \\ & | & \\ R^5-CH & & \\ & & \\ -N & & C- \\ | & & \| \\ H & & O \end{matrix} \quad (4)$$

where $R^5$ is as defined above; and $R^9$ is hydrogen; $C_{1-4}$ alkyl; hydroxy; or $C_{3-7}$ cycloalkyl; or (a) $Y-(\overset{R^{10}}{\overset{|}{CH}})_q-R^{11}$; (b) $Y-(\overset{R^{12}}{\overset{|}{CH}})_{q'}-R^{13}$; or (5)

(c) $Y-\underset{R^{14}}{\overset{|}{CH}}-R^{11}$ where Y is —NH— or —O—; q is 1–5; q' is 0–5; $R^{10}$ is hydrogen; hydroxy; $N(R')_2$, where R' may be the same or different and is hydrogen or $C_{1-4}$alkyl; guanidyl; or $N^{\oplus}(R')_3 A^{\ominus}$, where R' is as defined above, and $A^{\ominus}$ is a counterion; provided that at least one $R^{10}$ is not hydrogen; $R^{11}$ is $C_{1-4}$alkyl; $C_{3-7}$cycloalkyl; unsubstituted or mono- or disubstituted phenyl or naphthyl, wherein the substituents(s) is/are independently selected from the group consisting of $C_{1-6}$alkyl, trifluoromethyl, hydroxy, $C_{1-4}$alkoxy, amino, mono- or di-$C_{1-4}$alkylamino, amino $C_{1-4}$alkyl, mono-, di-, or tri-$C_{1-4}$alkylamino-$C_{1-4}$alkyl, halo, carboxy, carboxy ester or amide, carboxy-$C_{1-4}$alkoxy, carboxy-$C_{1-4}$alkoxy ester or amide, α-aminocarboxy-$C_{1-4}$alkyl, αaminocarboxy-$C_{1-4}$alkyl ester or amide, carboxy-$C_{1-4}$alkyl, carboxy-$C_{1-4}$alkyl ester or amide, guanidyl, and guanidyl-$C_{1-4}$alkyl; carboxy, ester or amide; sulfo; or an unsubstituted or mono- or disubstituted heterocycle, representing a 5- or 6-membered ring or benzofused 5- or 6-membered ring comprising one or two heteroatoms independently selected from N, O and S, where the substituent(s) is/are independently selected from the group consisting of $C_{1-6}$alkyl, hydroxy, trifluoromethyl, $C_{1-4}$alkoxy, halo, phenyl-$C_1$-$C_4$-alkyl, naphthyl-$C_1$-$C_4$-alkyl, amino, and mono- or di-$C_{1-4}$alkylamino; $R^{12}$ is hydrogen; or carboxy, ester or amide; $R^{13}$ is carboxy, ester or amide; sulfo; or aryl substituted with up to three members selected from the group consisting of amino-$C_{1-4}$alkyl, mono-, di-, or tri-$C_{1-4}$-alkylamino-$C_{1-4}$alkyl, halo, carboxy, carboxy ester or amide, carboxy-$C_{1-4}$alkoxy, carboxy-$C_{1-4}$alkoxy ester or amide, α-aminocarboxy-$C_{1-4}$alkyl, α-aminocarboxy-$C_{1-4}$alkyl ester or amide, carboxy-$C_{1-4}$alkyl, carboxy-$C_{1-4}$alkyl ester or amide, guanidyl, and guanidyl-$C_{1-4}$alkyl; and $R^{14}$ is carboxy, ester or amide; or (d) $Y(CH_2)_k\!-\!\!\bigcirc\!\!-\!(O)_{k'}(CH_2)_{k''}(O)_{k'''}\!-\!\underset{OR''}{\overset{O}{\overset{\|}{P}}}\!-\!OR';$ or (e) $Y(CH_2)_k\!-\!\!\bigcirc\!\!-\!(O)_{k'}(CH_2)_{k''}(O)_{k'''}\!-\!\underset{O}{\overset{O}{\overset{\|}{\underset{\|}{S}}}}\!-\!OR',$ where Y is —NH— or —O—; k is 0–4; k' is 0 or 1; k" is 0–4; k''' is 0 or 1; R' is hydrogen or $C_{1-4}$alkyl; and R" is hydrogen or $C_{1-4}$alkyl;

L is absent; OR"; NHR"; or $N(R")_2$, where R" may be the same or different and is hydrogen or $C_{1-4}$alkyl; provided that, B and/or L are/is present only when J is $$\begin{matrix} & R^9 & \\ & | & \\ R^5-CH & & \\ & & \\ -N & & C- \\ | & & \| \\ H & & O \end{matrix},$$

where $R^5$ and $R^9$ are as defined above;
$R^1$ is hydrogen; $C_{1-4}$ alkyl; hydroxy $C_{1-4}$alkyl; mono- or disubstituted pheny or naphthyl, where the substituent(s) is/are selected from the group consisting of $C_{1-4}$ alkyl, trifluoromethyl, hydroxy, $C_{1-4}$ alkoxy, and halo; indolyl; 4-imidazolyl; amino $C_{2-4}$-alkyl; acyl-$C_{2-4}$-alkyl wherein the acyl is $R^9-\overset{O}{\overset{\|}{C}}-$ and $R^9$ is as defined above; guanidyl $C_{2-3}$-alkyl; or methylthiomethyl;
$R^4$ is hydrogen; or $\underset{R^3}{\overset{|}{CH}}-R^9,$ where $R^9$ is as defined above; and $R^3$ is hydrogen; $C_{1-4}$alkyl; indolyl; or unsubstituted or mono- or disubstituted phenyl, naphthyl, phenyl-$C_1$-$C_4$alkyl, or naphthyl-$C_1$-$C_4$alkyl, wherein the substituent(s) is/are selected from the group consisting of $C_{1-4}$alkyl, trifluoromethyl, hydroxy, $C_{1-4}$alkoxy, and halo; and wherein all of the asymmetric carbon atoms have an S configuration, except for those in the B and D substituents, which may have an S or R configuration, and the G group, which must have a 2R,3S,4S configuration; and a pharmaceutically acceptable salt thereof.

2. A peptide according to claim 1 wherein the peptide is a member selected from the group consisting essentially of:

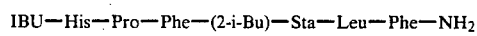

IBU—His—Pro—Phe—(2-i-Bu)—Sta—Leu—Phe—NH₂

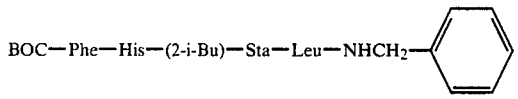

BOC—Phe—His—(2-i-Bu)—Sta—Leu—NHCH₂—

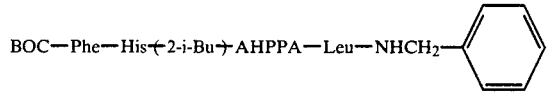

BOC—Phe—His(2-i-Bu)AHPPA—Leu—NHCH₂—

BOC—Phe—His(2-i-Pent)AHPPA—Leu—NHCH₂—

3. A pharmaceutical composition comprising a pharmaceutical carrier and a therapeutically effective amount of a peptide according to claim 1.

4. A composition according to claim 3 wherein the peptide is a member selected from the group consisting essentially of:

IBU—His—Pro—Phe—(2-i-Bu)—Sta—Leu—Phe—NH₂

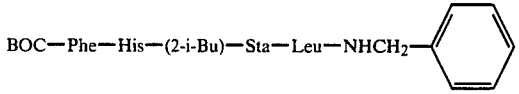

BOC—Phe—His—(2-i-Bu)—Sta—Leu—NHCH₂—

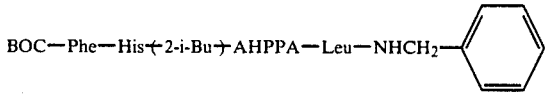

BOC—Phe—His(2-i-Bu)AHPPA—Leu—NHCH₂—

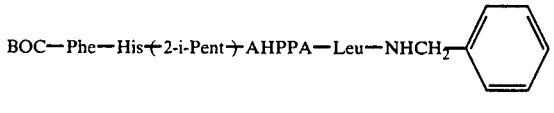

BOC—Phe—His(2-i-Pent)AHPPA—Leu—NHCH₂—

* * * * *

UNITED STATES PATENT AND TRADEMARK OFFICE
CERTIFICATE OF CORRECTION

PATENT NO.   : 4,663,310

DATED        : May 5, 1987

INVENTOR(S)  : Bock, et al

It is certified that error appears in the above-identified patent and that said Letters Patent is hereby corrected as shown below:

In the Claims:

Col. 31, line 17, Claim 2 change "IBU-His-Pro-Phe-(2-i-Bu)-Sta-Leu-Phe-$NH_2$" to -- IBU-His-Pro-Phe-Phe-(2-i-Bu)-Sta-Leu-Phe-$NH_2$ --.

Col. 32, line 15, Claim 4 change "IBU-His-Pro-Phe-(2-i-Bu)-Sta-Leu-Phe-$NH_2$" to -- IBU-His-Pro-Phe-Phe-(2-i-Bu)-Sta-Leu-Phe-$NH_2$ --.

Signed and Sealed this

Twentieth Day of October, 1987

Attest:

DONALD J. QUIGG

Attesting Officer

Commissioner of Patents and Trademarks